US009283153B2

(12) United States Patent
Osswald et al.

(10) Patent No.: US 9,283,153 B2
(45) Date of Patent: Mar. 15, 2016

(54) CURABLE COMPOSITION WITH SHORTENED SETTING TIME, PROCESS OF PRODUCTION AND USE THEREOF

(75) Inventors: Peter U. Osswald, Tuerkheim (DE); Henning Hoffmann, Windach (DE); Joachim W. Zech, Kaufering (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 8 days.

(21) Appl. No.: 14/237,502

(22) PCT Filed: Aug. 10, 2012

(86) PCT No.: PCT/US2012/050315
§ 371 (c)(1),
(2), (4) Date: Mar. 18, 2014

(87) PCT Pub. No.: WO2013/025494
PCT Pub. Date: Feb. 21, 2013

(65) Prior Publication Data
US 2014/0228473 A1 Aug. 14, 2014

(30) Foreign Application Priority Data
Aug. 12, 2011 (EP) .................... 11177383

(51) Int. Cl.
A61K 6/10 (2006.01)
A61K 6/083 (2006.01)

(52) U.S. Cl.
CPC .. A61K 6/10 (2013.01); A61K 6/083 (2013.01)

(58) Field of Classification Search
USPC .......................... 523/109; 433/214
See application file for complete search history.

(56) References Cited

U.S. PATENT DOCUMENTS

| 3,715,334 | A | 2/1973 | Karstedt |
|---|---|---|---|
| 3,775,352 | A | 11/1973 | Leonard |
| 3,814,730 | A | 6/1974 | Karstedt |
| 3,933,880 | A | 1/1976 | Bergstrom |
| 4,035,453 | A | 7/1977 | Hittmair |
| 4,096,159 | A | 6/1978 | Hechtl |
| 4,273,902 | A | 6/1981 | Tomioka |
| 4,657,959 | A | 4/1987 | Bryan |
| 4,782,101 | A | 11/1988 | Waller |
| 5,249,862 | A | 10/1993 | Herold |
| 5,286,105 | A | 2/1994 | Herold |
| 5,332,122 | A | 7/1994 | Herold |
| 5,380,812 | A | 1/1995 | Lutz |
| 5,403,885 | A | 4/1995 | Voigt |
| 5,464,131 | A | 11/1995 | Keller |
| 5,569,691 | A | 10/1996 | Guggenberger |
| 5,684,060 | A | 11/1997 | Konings |
| 5,750,589 | A | 5/1998 | Zech |
| 5,924,600 | A | 7/1999 | Keller |
| 6,135,631 | A | 10/2000 | Keller |
| 6,244,740 | B1 | 6/2001 | Wagner |
| 6,677,393 | B1 | 1/2004 | Zech |
| 7,572,842 | B2 | 8/2009 | Zech |
| 7,700,712 | B2 | 4/2010 | Zech |
| 2004/0085854 | A1 | 5/2004 | Pauser |
| 2005/0171233 | A1 | 8/2005 | Bublewitz |
| 2005/0250871 | A1 | 11/2005 | Bublewitz |
| 2007/0060717 | A1 | 3/2007 | Zech |
| 2010/0292362 | A1 | 11/2010 | Zech |

FOREIGN PATENT DOCUMENTS

| EP | 0231420 | 8/1987 |
|---|---|---|
| EP | 0232733 | 8/1987 |
| EP | 0480238 | 4/1992 |
| EP | 0522341 | 1/1993 |
| EP | 0662490 | 7/1995 |
| EP | 0730913 | 9/1996 |
| EP | 0863088 | 9/1998 |
| EP | 1353625 | 10/2003 |
| EP | 1475069 | 11/2004 |
| EP | 1502572 | 2/2005 |
| EP | 1290998 | 3/2005 |
| EP | 1512724 | 3/2005 |
| EP | 1741420 | 1/2007 |
| EP | 2 072 029 | 12/2007 |
| WO | WO 02-058641 | 8/2002 |
| WO | WO 2007-001896 | 1/2007 |

OTHER PUBLICATIONS

International Search Report for PCT International Application No. PCT/US2012/050315 Mailed on Nov. 27, 2012, 7 pages.

Primary Examiner — Tae H Yoon

(57) ABSTRACT

The invention relates to a curable dental composition being prepared by mixing a base paste and a catalyst paste, "the base paste comprising component(s) (A) with curable moieties (AC)," the catalyst paste comprising a catalyst (C) being able to initiate or catalyse a crosslinking reaction involving components (A) upon mixing base paste and catalyst paste, the curable composition comprising a component (X) with reactive moieties, component (X) being either produced during the curing reaction or being present in either the base paste or the catalyst paste before the crosslinking reaction is initiated or catalysed, component X being different from component (s) (A), either base paste or catalyst paste comprising a reactant (Y), reactant (Y) being able to interact with component (X), but not taking part in the crosslinking reaction, the curable composition being able to produce energy in an amount sufficient to increase the temperature T1 of the composition being present 20 s after mixing the base paste and the catalyst paste to a temperature T2 being from about 6 to about 20° C. above T1.

13 Claims, 1 Drawing Sheet

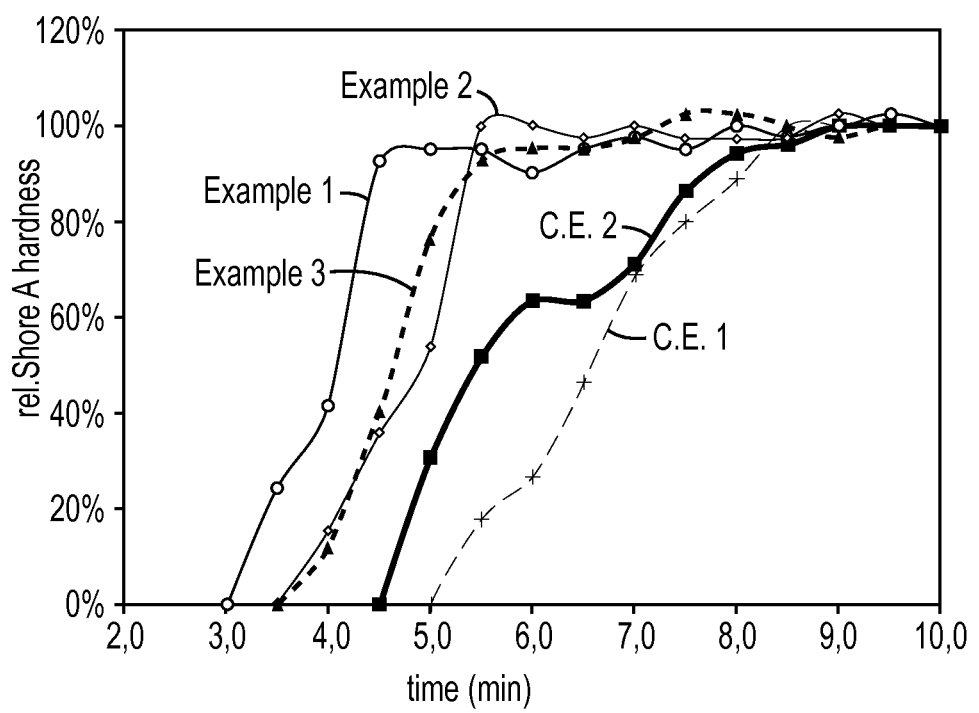

US 9,283,153 B2

CURABLE COMPOSITION WITH SHORTENED SETTING TIME, PROCESS OF PRODUCTION AND USE THEREOF

This application is a 35 U.S.C. §371 National Stage application of International Application No. PCT/US2012/05315, with an International Filing Date of Aug. 10, 2012, which claims priority to EP Application No. 11177383.4, filed Aug. 12, 2011.

FIELD OF THE INVENTION

The invention relates to a curable composition with a shortened setting time, its process of production and use thereof. Such a composition can especially be useful in the dental field.

BACKGROUND ART

Addition crosslinked silicone materials typically comprise a divinyl terminated polydimethylsiloxane, a polydimethylsiloxane containing at least 3 SiH-groups per molecule, a Pt-based catalyst and optionally fillers, retarders and other typically used auxiliaries.

For the control of the setting reaction short-chained divinylsiloxanes, as e.g. divinyltetramethyldisiloxane, are typically applied as retarders (see e.g. U.S. Pat. No. 4,096,159, U.S. Pat. No. 5,403,885 and US 2005/0171233). Further components which can be used are alkynes or alkynols as described e.g. in EP 1 741 420 A1. Other components for retarding the hydrosilylation reaction are molecules or compounds which are capable of forming complexes with the platinum catalyst, as e.g. phosphorus compounds, as known from high temperature addition-curable silicone compositions (e.g. as described in U.S. Pat. No. 5,380,812).

Allyl- and methallylsilanes as hydrogen scavengers in addition cured silicone impression materials are described in U.S. Pat. No. 7,700,712 and the use of di, -tri-, and tetraallylsilane for increasing the crosslinking density of impression materials are described in US 2007/0060717.

Dental silicone-based impression materials comprising an addition- and condensation-curing mechanism are described e.g. in WO 2002/058641 and U.S. Pat. No. 7,572,842.

SUMMARY

It would be desirable to provide a curable dental composition which shows an improved curing behaviour compared to commercially available curable dental compositions.

Alternatively or in addition if possible, it would be desirable to provide a curable dental composition which has a sufficiently long working time but a reduced curing or setting time.

Alternatively or in addition if possible, the cured dental composition should be homogeneous and not contain gas bubbles which may have been produced during the hardening reaction.

If the dental composition is used for making dental impressions, it would also be desirable, that a gypsum cast of the impression should be essentially free of voids, which e.g. might be caused by gas evolution (e.g. hydrogen) on the surface of the cured dental impression material once contacted with an aqueous gypsum suspension.

It was found that at least one of the above mentioned objects can be achieved, e.g. by including in the curable composition a system being able to generate energy (e.g. heat), thus providing a self-warming composition.

In one embodiment the invention features a curable composition comprising a base paste and a catalyst paste,
the base paste comprising component(s) (A) with curable moieties (AC),
the catalyst paste comprising a catalyst (C) being able to initiate or catalyse a crosslinking reaction involving components (A) upon mixing base paste and catalyst paste,
the curable composition comprising a component (X) with reactive moieties,
component (X) being either produced during the curing reaction or being present in either the base paste or the catalyst paste before the crosslinking reaction is initiated or catalysed, component X being different from component(s) (A),
either base paste or catalyst paste comprising a reactant (Y),
reactant (Y) being able to interact with component (X), but not taking part in the crosslinking reaction,
the curable composition being able to produce energy in an amount sufficient to increase the temperature T1 of the composition being present 20 s or 30 s or 1 min after mixing the base paste and the catalyst paste to a temperature T2 being from about 6 to about 20° C. above T1.

The invention is also directed to a curable dental composition being prepared by mixing a base paste and a catalyst paste,
the base paste comprising component(s) (A) with curable moieties (AC) selected from a combination of at least one organopolysiloxane with at least 2 aliphatically unsaturated groups and at least a component comprising Si—H moieties,
the catalyst paste comprising a catalyst (C) comprising a Pt containing component,
the curable composition comprising a component (X) comprising at least one Si—H group as reactive moiety,
either base paste or catalyst paste comprising a reactant (Y), reactant (Y) being able to interact with component (X), but not taking part in a crosslinking reaction,
reactant (Y) being selected from a silane component with only one unsaturated moiety, an alkyl vinyl ether component, an alkyl allyl ether component and mixtures thereof,
the curable composition being able to produce energy in an amount sufficient to increase the temperature T1 of the composition being present 20 s after mixing the base paste and the catalyst paste to a temperature T2 being from about 6 to about 20° C. above T1.

The invention is further directed to a curable dental composition being prepared by mixing a base paste and a catalyst paste,
the base paste comprising component(s) (A) with curable moieties (AC) selected from a combination of at least one organopolysiloxane with at least 2 aliphatically unsaturated groups and at least a component comprising Si—H moieties,
the catalyst paste comprising a catalyst (C) comprising a Pt containing component,
the curable composition comprising a component (X) comprising at least one Si—H group as reactive moiety,
either base paste or catalyst paste comprising a reactant (Y), reactant (Y) being able to interact with component (X), but not taking part in the crosslinking reaction,
reactant (Y) being selected from a silane component with only one unsaturated moiety, an alkyl vinyl ether component, an alkyl allyl ether component and mixtures thereof.

A further embodiment of the invention is directed to a process of producing a dental impression material, the process comprising the step of mixing base paste and catalyst paste, base paste and catalyst paste being as described as in the present text, the mixture of base paste and catalyst paste having a temperature T1 measured 20 s after mixing, the mixture of base paste and catalyst paste having a temperature T2 measured within a time frame of 15 min after mixing, T2 being from about 6 to about 20° C. above T1.

In another embodiment, the invention relates to the use of a component (X) for shortening the curing time of a curable composition being present in the form of a base paste and a catalyst paste, base paste, catalyst paste and component (X) being as described in the present text.

BRIEF DESCRIPTION OF FIGURES

FIG. 1 shows the development of the Shore hardness A of curable compositions after mixing a base paste A and a catalyst paste B over time.

Within the description of the invention, the following terms are defined as follows:

The term "compound or component" is a chemical substance which has a particular molecular identity or is made of a mixture of such substances, e.g., polymeric substances.

A "curable composition" may be described as the components of a composition contributing to the formation of a network due to chemical interaction (e.g. formation of chemical bondings) between the components thereby leading to a significant change in rheological properties like viscosity.

The terms "vulcanizing, hardening, crosslinking, setting" are used interchangeable and refer to compounds that have as a common attribute the development of a crosslinked elastomer from relatively low molecular weight linear or branched polymers by means of a chemical reaction that simultaneously forms these crosslinks and effectively extends chain length at room temperature. "Room temperature vulcanizing" implies that the curing reaction can proceed at temperatures at or near 25° C. For example, the oral cavity of the mouth has an average temperature of approximately 32° C. and is therefore near room temperature. Certain "high temperature curable materials" are designed to cure only at relatively high temperatures (e.g., >50° C. or >100° C.) and are stable (i.e., the curing reaction is retarded) at room temperature for prolonged periods.

The term "crosslinked, cured or hardened composition" as used herein, refers to a material that is obtained by reaction of the functional group or groups of curable components to lengthen them and connect them, e.g., to form a crosslinked network.

The term "crosslinker" refers to polymers that react with the functional group or groups of the polymer chains simultaneously to lengthen them and connect them laterally, e.g., to form the crosslinked network characteristic of a silicone elastomer. In contrast to a thermoplastic polymer (i.e., a polymer that softens and flows upon heating) a crosslinked polymer, after crosslinking, is incapable characteristically of further flow. Crosslinkers typically comprise at least 3 functional or reactive moieties being able to undergo a crosslinking reaction.

The term "hydrosilation" means the addition of an organosilicone hydride compound to a compound containing an aliphatic multiple bond (e.g., an olefinic or acetylenic unsaturation), preferably a vinyl group, —CH=$CH_2$.

By "paste" is meant a soft, viscous mass of solids dispersed in a liquid.

The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound.

"Polyether" or "polyether group containing compound" are compounds having a molecular weight of at least about 150 g/mol and containing in the backbone at least about 3, 10 or 20 ether moieties. Polyether containing compositions used as dental impression material can be cured by different mechanisms.

The term "molecular weight" refers to the number average of the molecular weight, as is conventionally determined for the individual classes of polymers by gel permeation chromatography (GPC) against a standard of defined molecular weight. Suitable measurement methods will be known to the person skilled in the art.

Furthermore, the determination of the molecular weights and the molecular weight distribution of polymeric polyols can be carried out, for example, by means of end group determination, for example by nuclear magnetic resonance (NMR) methods. Also suitable for the determination of the molecular weights and the molecular weight distribution of polymeric polyols is the determination of the hydroxyl value.

The term "working time" as used herein, refers to the time between the initiation of the setting reaction (e.g., when the vinyl-containing organopolysiloxane, the organohydropolysiloxane, and the platinum catalyst are mixed) and the time the setting reaction has proceeded to the point at which it is no longer practical to perform further physical work upon the system, e.g., reform it, for its intended purpose. When the reaction has proceeded to this later point, the material is said to have reached its "gel point." The working time preferably provides enough time to mix and place the composition into its desired form. For many dental impression compositions and applications the working time under conditions of use can be greater than about 30 s (seconds), or greater than about 1 min (minute), or greater than about 2 min. Thus, the working time is typically within a range of about 30 s to about 3 min or about 1 min to about 2 min. So-called "fast-setting" compositions typically have a shorter working time, e.g. less than about 2 min or less than about 1.5 min.

The terms "set time" or "setting time" as used herein, refer to the time at which sufficient curing has occurred so that essentially the material's final cured-state properties are obtained. For a silicone impression material the set time is that time at which one may remove the material from the surface being replicated without causing permanent deformation of the silicone material. The setting time may be approximated, e.g., by measuring the torque of the reacting composition on an oscillatory rheometer. When the torque value reaches a maximum value the material is said to be fully set. An arbitrary torque value which is less than the typical maximum value (e.g. 90% of the maximum value) may alternatively be used as a practical approximation of the set time. In general, shorter setting times are preferred over longer setting times. For dental impression compositions the setting time occurs at a time preferably less than about 10 min after initiation of the reaction. More preferably the setting time is less than the sum of about 5 min plus the working time. Most preferably the setting time is just longer than the desired working time.

More specifically, for dental impression materials the setting time is the time between positioning of the spoon with the dental impression material in the mouth of the patient and removal of the cured material, and can also be called the mouth residence time or period. Setting times of less than about 5 min mouth residence time, preferably less than about 4 min, and particularly preferably less than about 3 min are desirable properties for the dentist working with situation impression materials. For example, the one-phase impression material Imprint™ (3M ESPE) has a setting time of about 5 minutes, while a typical alginate impression material such as Palgat™ (3M ESPE) has a setting time of about 4 min.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is carried out by placing a liquid material into the mouth in a customised tray. The material then sets to become an elastic solid, and when removed from the mouth retains the shape of the teeth. Common materials used for dental impressions are sodium alginate, agar, polyethers including aziridine substituted polyether materials and silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

The term "automixer-suitable impression material" relates to a multi-component impression material which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™" and "Pentamix™ 2" devices of 3M ESPE Company (cf. U.S. Pat. No. 5,286,105 and U.S. Pat. No. 5,249,862).

A "dental compositions and dental articles" within the meaning of the present invention is a composition which is to be used in the dental field (including restorative and prosthodontic work) including the orthodontic area. In this respect, a dental composition typically does not contain hazardous substances. Commercially available products have to fulfil certain requirements such as those given in ISO 4823. Typically, those compositions cure or set at ambient conditions.

By a "temporary or long term crown and bridge material" is meant a material, which is used for the preparation of dental crowns and bridges containing hardenable monomers, including (meth)acrylates. These materials are typically used during the time period needed for making a permanent restoration. A typical time period ranges from a few days (e.g. 3 to 5) over weeks (1 to 3) to a few months (1 to 6). A long term crown and bridge material is typically used over a time period of about 6 to about 24 months.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about."

DETAILED DESCRIPTION OF THE INVENTION

The invention relates to a hardenable composition containing a (further) system being able to generate energy (e.g. heat). Due to the energy generation, the hardening reaction of the curable composition obtained after mixing the base and the catalyst paste is typically accelerated. If desired, this can be determined by measuring the increase of the Shore hardness over time.

This allows for the provision of a composition having a decreased setting time, whereas the working time remains essentially unchanged.

If was also found that the warming of the composition during the setting reaction is still in a range which is acceptable to a patient, when a dental impressioning procedure is conducted.

On the one hand, the warming of the composition should be sufficient to accelerate the setting reaction, on the other hand, the temperature shall not exceed a range which could be damaging to the patient's health or cause pain.

Due to the presence of reactant (Y), the curable composition is able to generate heat essentially independent and in addition to energy which might be produced during the crosslinking reaction involving component (A).

The energy produced is typically sufficient to increase the temperature T1 of the composition being present 20 s after mixing the base paste and the catalyst paste to a temperature T2 being from about 6 to about 20° C. or above about 7 to about 15° C. or above 8 to above 12° C. above T1.

The composition can be used especially in the dental and orthodontic field, e.g. as a dental impression material, for taking dental impressions and/or for producing a dental impression material.

According to one embodiment, the hardenable composition can be characterized by at least one of the following parameters:
  a consistency (according to ISO 4823) of 0 or 1 (corresponding to at most 35 mm) or 2 (corresponding to 31 mm to 41 mm) or 3 (corresponding to at least 36 mm), preferably 2; and/or
  a setting time within about 15 or about 10 or about 8 or about 6 or about 5 or about 4 min after mixing at ambient conditions (e.g. about 23° C.).

That is, the curable composition can show a comparable low viscous behaviour (consistency 3), a medium or heavy viscosity (consistency 1 or 2) or show a putty-like behaviour (consistency 0).

If desired, the setting time data can be measured as described in the Examples section below.

According to another embodiment, the hardened or cured composition shows at least one of the following parameters:
  a tensile strength (according to DIN 53504) of about 0.1 to about 5 MPa or about 0.2 to about 4 MPa or 0.3 to about 3 MPa,
  an elongation at break (according to DIN 53 504) of about 10 to about 300% or about 15 to about 200%, or about 20 to about 100%,
  a Shore hardness A (according to IN 53 505) of about 15 to about 75, or about 30 to about 60,
  a recovery from deformation (according to ISO 4823): at least about 90%, or at least about 95%, or at least about 98%,
  a density (according to the Archimedes method; weight of 1 ml cured composition) of the composition of about 0.8 to about 2 g/ml or about 1 to about 1.8 g/ml.

The curable composition of the invention comprises a base paste and a catalyst paste.

The base paste comprises components (A) with curable moieties (AC).

Hardening of components (A) comprising curable moieties (AC) can be achieved by different mechanisms.

Generally, polyaddition and polycondensation are preferred types of polymerization reactions, wherein polyaddition polymerization is sometimes preferred. These curing mechanisms are described in further detail below.

The curable moieties (AC) of components (A) include alkoxy (including C1 to C8 alkyl) silyl groups, silanol groups, vinyl groups, ally groups, (meth)acrylate groups, mixtures and combinations thereof.

Besides curable moieties (AC), components (A) can contain polyether, polyester, polyacetal, polyurethane or polysiloxane moieties or a mixture of two or more of these moieties. These moieties typically form the backbone or at least a part of the backbone of components (A).

Appropriate polyethers can be produced in a manner known to the person skilled in the art by the reaction of the starting compound having a reactive hydrogen atom with alkylene oxides. Suitable polyethers, which can be used, include those which meet the requirements in terms of material properties with regard to the preferred use as dental materials. Especially suitable are polyether compounds which are obtainable by polyaddition of ethylene oxide, 1,2-propylene oxide, 1,2-butylene oxide, styrene oxide, epichlorohydrin or tetrahydrofuran or mixtures of two or more of the mentioned compounds with the aid of a suitable starting compound and a suitable catalyst.

Suitable polyesters, which can be used, include those obtainable by polycondensation of dicarboxylic acids with diols or by polycondensation of oxycarboxylic acids having a substantially linear structure.

Polyacetals can also be suitable as polyol condensation products. Polyacetals are sometimes understood to be compounds obtainable by reacting glycols, e.g. diethylene glycol or hexanediol or a mixture thereof, with formaldehyde. Polyacetals, which can be used in the context of the invention, may also be obtained by the polymerisation of cyclic acetals.

Suitable polyurethanes, which can be used, include those which can be prepared by the reaction of polyols or polycarboxylic acids and isocyanates. Appropriate preparation methods are known to the person skilled in the art. Suitable polyols have already been described in the context of the present text as starting materials for the preparation of polyesters.

Hardening of the curable composition might be effected e.g. by a polycondensation reaction.

A typical curing mechanism can be based upon a polycondensation reaction of alkoxy silyl groups which might take place in the presence of an acidic catalyst or salt of a strong acid and water.

The curing mechanism can also be based upon a polycondensation reaction of alkoxy silyl groups with silanol groups in the presence of a catalyst without water.

Comprised are also alkoxy functionalized polyethers crosslinking via a condensation reaction as described in US 2005/250871.

Hardening of the curable composition can also be effected by a polyaddition reaction.

This curing mechanism is typically based upon the polyaddition of silanes with olefinically unsaturated double bonds (e.g. vinyl groups) in the presence of a catalyst, such as a Pt containing compound. This curing mechanism is known for a long time. The respective compositions are often referred to as VPS materials.

According to this embodiment, the invention features a composition comprising as components (A) at least one organopolysiloxane with at least 2 aliphatically unsaturated groups.

The organopolysiloxane with at least two pendant or terminal triorganosiloxy groups is a molecule in which at least one of the three organic groups is a group with an ethylenically unsaturated double bond. Generally, the groups with an ethylenically unsaturated double bond can be located on any monomeric unit of the organopolysiloxane. It can, however, be preferred, that the groups with an ethylenically unsaturated double bond are located on or at least near the terminal, monomeric units of the polymer chain of the organopolysiloxane. In another embodiment, at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this general structure are represented by the following formula

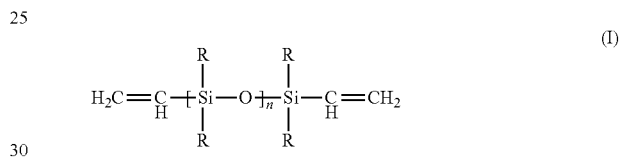

(I)

in which the radicals R, independently from each other, represent a non-substituted or substituted, monovalent hydrocarbon group with 1 to about 6 C atoms, which is preferably free from aliphatic multiple bonds and where n generally can be chosen such that the viscosity of the organopolysiloxanes lies between about 4 and about 1,000,000 mPas or between about 6 and about 500,000 or between about 10 and about 100,000 mPas. The parameter n can, e.g., be in the range of about 10 to about 10,000.

Generally, the radicals R in the above formula can represent any non-substituted or substituted, monovalent hydrocarbon group with 1 to about 6 C atoms. Non-substituted or substituted, monovalent hydrocarbon groups with 1 to about 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product.

The term "detrimental" as used in the context of the present text relates to a change of properties of the precursors or the cured product that negatively affect the usefulness of the precursors or the cured product in their intended use.

In another embodiment of the invention, at least about 50% of the radicals R are methyl groups. Examples of other radicals R that can be present in the organopolysiloxanes according to the above formula are ethyl, propyl, isopropyl, n-butyl, tert-butyl, the pentyl isomers, the hexyl isomers, vinyl, propenyl, isopropenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially regarding the above mentioned molecules, their chemical constitution and their preparation, is expressly regarded as being part of the disclosure of the present document and is included herein by reference.

The preparation of molecules according to the above-mentioned formula would generally be understood by the skilled person based upon the teachings of the prior art regarding similar molecules. Particularly preferred are linear polydimethylsiloxanes according to the above formula having viscosities within the specified viscosity ranges and end groups comprising dimethylvinylsiloxy units and methyl groups as the radicals R.

A component (A) which can be employed can consist of one type (A1) of organopolysiloxane. The organopolysiloxane can have a viscosity starting in the range of about 5 to about 1,000,000 mPas, or about 10 to about 500,000 mPas or about 20 to about 50,000 or about 30 to about 40,000 mPas.

It is, however, also possible that component (A) comprises two or more constituents, (A1), (A2) and so on, which can differ, e.g., in the chemical composition of their backbone, or their molecular weight, or their substituents or their viscosity, or any other differentiating feature or two or more of the above mentioned features.

In one embodiment the difference in viscosities of different constituents of component (A) can be higher than a factor of 2, e.g., higher than a factor of about 5, higher than a factor of about 10, higher than a factor of about 20, higher than a factor of about 30, higher than a factor of about 40, higher than a factor of about 50, higher than a factor of about 60, higher than a factor of about 70, higher than a factor of about 80, higher than a factor of about 90 or higher than a factor of about 100. The difference in viscosities can be even higher, e.g., higher than a factor of about 200, higher than a factor of about 300, higher than a factor of about 500, higher than a factor of about 800, higher than a factor of about 1,000 or higher than a factor of about 5,000, it should, however, preferably not exceed a value higher than a factor of about 10,000. It should be kept in mind that the values mentioned above relate to a factor for the difference in viscosities, not the viscosity values themselves.

If desired, the viscosity can be measured using a Haake Rotovisco RV20 device (spindle MV, measuring cup NV). The viscosity is typically measured at 23° C. After activation and rectification of the system, spindle MV is installed. Then the material to be measured is filled into the measuring cup NV. Without undue delay, the spindle is lowered into the measuring cup NV. The spindle should be covered by a layer of the material of a maximum thickness of 1 mm. The material to be measured is tempered for 20 min at 23° C. The measurement is started by starting the spindle to turn and the viscosity values (mPas) are recorded starting 20 s after the start of measurement. Care must be exercised to ensure that the measuring cup NV does not rotate or move at any time. A value for the viscosity is obtained in mPas. The above mentioned method of measurement corresponds to DIN 53018-1.

If component (A) contains constituents of different viscosities, the ratio of the amount of constituent with the lowest viscosity to the amount of constituent with the highest viscosity can be chosen relatively freely, depending on the desired properties of the precursors and the cured resin. It can, however, be advantageous when the ratio of the amount of constituent with the lowest viscosity to the amount of constituent with the highest viscosity is within a range of from about 1:20 to about 20:1, especially about 1:10 to about 10:1 or about 1:5 to about 5:1. Good results can e.g. be obtained with ratios of from about 1:3 to about 3:1 or about 1:2 to about 2:1. It can furthermore be adequate in some cases, when the amount of constituent with the highest viscosity is about equal to or higher than the amount of constituent with the lowest viscosity, resulting in a value of from about 0.9:1 to about 3:1 for the ratio of the amount of constituent with the highest viscosity to the amount of constituent with the lowest viscosity. All of the ratios are based on the weight of the constituents.

With respect to the above mentioned embodiment, the composition typically also contains an organohydrogenpolysiloxane with at least 2 or 3 Si-bonded hydrogen atoms (i.e. Si—H moieties) per molecule.

These component(s) may also function as component (X). However, if component (X) corresponds to the organohydrogenpolysiloxane used for the crosslinking reaction, the organohydrogenpolysiloxane is used in excess.

Thus, component (X) can be same or different as the Si—H group(s) containing components being present in the base paste of a curable composition hardening by a polyaddition reaction.

By definition, an organohydrogenpolysiloxane according to the present text does not belong to the group of organopolysiloxanes as described in the context of the invention.

An organohydrogenpolysiloxane according to the invention typically contains about 0.01 to about 1.7 wt.-% silicon-bonded hydrogen or about 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least about 50%, preferably about 100%, of the hydrocarbon radicals R that are bonded to silicon atoms are methyl radicals.

The organohydrogenpolysiloxanes may have a viscosity of about 10 to about 1,000 mPas or from about 15 to about 550 mPas or from about 20 to about 150 mPas.

Besides curable components (A), the curable composition may also contain organopolysiloxanes without reactive substituents. Non-reactive substituents include those which do not co-polymerize with the other components of the composition during the hardening process. These are preferably linear, branched or cyclic organopolysiloxanes where all silicon atoms are surrounded by oxygen atoms or monovalent hydrocarbon radicals with 1 to 18 carbon atoms which can be substituted or non-substituted. The hydrocarbon radicals can be methyl, ethyl, $C_2$-$C_{10}$ aliphatics, trifluoropropyl groups as well as aromatic $C_6$-$C_{12}$ radicals.

Polydimethylsiloxanes with trimethylsiloxy end groups can be preferred and can be used in an amount of about 0 to about 40 wt.-%, or about 0.1 to about 20 wt.-% or about 0.5 to about 10 wt.-% with respect to the whole composition.

The inventive composition also contains a catalyst.

The nature of the catalyst to be used typically depends on the nature of the components (A) comprising curable moieties (AC) used.

With respect to addition curable compositions, the catalyst is typically a platinum catalyst or a platinum containing catalyst, including a platinum complex which can be prepared from hexachloroplatinum acid by reduction with tetramethyldivinyldisiloxane. Such compounds are known to the skilled person and are wildly used in this field.

Any other platinum compounds which catalyze or accelerate addition cross-linking of silanes with ethylenically unsaturated double bonds are also suitable. Platinum-siloxane complexes as described, e.g. in U.S. Pat. No. 3,715,334, U.S. Pat. No. 3,775,352 and U.S. Pat. No. 3,814,730 are suitable. The disclosure of these patents with regard to platinum complexes and their preparation is explicitly mentioned and expressly regarded as part of the disclosure of the present text.

The catalyst can typically be used in an amount of about 0.00005 to about 0.05 wt.-%, particularly about 0.0002 to about 0.04 wt.-%, each calculated as elemental platinum and related to the overall weight of the composition.

With respect to condensation curable composition, the catalyst is typically an acid and metal organic compounds.

Examples of suitable acids or acidic catalysts which can be used include organo zinc compounds, titanates, zirconates such as for example tetraethyltitanate, tetraisopropyltitanate, tetra-n-propyltitanate, tetra-n-butyltitanate, dioctylzincdilaurate, dibutylzincdilaurate, tetra-n-butylzirconate and tetra-n-propylzirconate and mixtures thereof.

Typical ranges for these kinds of initiators include from about 0.005 wt.-% to about 35 wt.-% or from about 0.01 wt.-% to about 20 wt.-%, wt.-% with respect to the weight of the whole composition.

The inventive composition is typically able to produce energy during the curing reaction in an amount sufficient to increase the temperature from a level T1 to a level T2 after mixing the base paste and the catalyst paste.

This increase of temperature is mainly or partially caused by the reaction between component (X) and reactant (Y).

Component (X) may be produced during the curing reaction, or is present in either the base paste or the catalyst paste before the crosslinking reaction is initiated or catalysed. It is, however, also possible that at least two different components (X) are present or are generated and take part in the reaction. So, one component (X1) might be produced during the curing reaction and one component (X2) might already be present in the composition before starting or initiating the setting process.

Component (X) comprises at least one reactive moiety and is able to interact with reactant (Y).

Reactive moieties include —OH, Si—H, —OR (e.g. C1 to C4 alkyl) and combinations thereof.

The term "interact" includes chemical and physical interaction.

So, it is possible that component (X) forms chemical bonding(s) with reactant (Y). However, it is also possible that component (X) is absorbed by or adheres to the surface of reactant (Y).

Besides the interaction with reactant (Y), component (X) may also react with other component(s) being present in the composition.

If component (X) participates also in the crosslinking reaction with component (A), component (X) is used in excess with respect to reactant (Y). Then it can be assured that there are enough reactive moieties of component (X) present in the composition for generating energy which promotes an accelerated setting reaction.

The interaction of reactant (Y), however, is typically limited to an interaction with component (X).

Component (X) and reactant (Y) interact with each other in such a way that energy (especially heat) is produced. The amount of energy or heat produced is sufficient to warm up the composition from a temperature level T1 (measured e.g. 20 s after mixing) to a temperature level T2 (measured within a time frame of about 15 min after mixing). The temperature T2 is typically at least about 6, 7, 8, 9 or 10° C. above the temperature T1.

A typical temperature increase is in a range from about 6 to about 20° C. or from about 7 to about 15° C.

The temperature T1 is typically in a range of about 15° C. to about 35° C. or from about 23° C. to about 30° C.

The temperature T2 should typically be below about 50° C. or below about 40° C. or below about 36° C.

If desired, the temperature increase can be determined as described in the Examples section.

With respect to curable compositions hardening by a polycondensation reactions, typical examples for component (X) include water, alcohols (including methanol, ethanol, n- and i-propanol) and mixtures thereof.

With respect to curable compositions hardening by a polyaddition reactions, especially a polyaddition reaction involving vinyl terminated polydimethylsiloxane(s) and poly(methyl)(hydrogen)siloxane(s), typical examples for component (X) include silanes and siloxanes with at least one or two SiH moiety(ies) like poly(methyl)(hydrogen)siloxane(s) and mixtures thereof.

Reactant (Y) can typically be characterized by at least one of the following features:
  Molecular weight: from about 50 to about 1,000 or from about 100 to about 800 or from about 100 to about 500, or from about 100 to about 300.
  Being solid or liquid at room temperature (23° C.).
  Reactant (Y) is typically present in an amount of at least about 0.5 wt.-% or at least about 1 wt.-1% or at least about 1.25 wt.-% with respect to the whole composition.
  Ratio of component (X) to reactant (Y): at least about 1:1 or at least about 6:1 or at least about 8:1 or at least about 10:1 with respect to weight. Typical ranges include from about 6:1 to 20:1 or from about 8:1 to about 15:1 with respect to weight.

It was found that adjusting the molar ratio of the reactive moieties being present in component (X) to reactant (Y) to a range from about 1.1 to about 5 or from about 1.2 to about 4.8 or from about 1.25 to about 4.5 can be beneficial for achieving the desired effect(s).

If either of the above features is not fulfilled, it might be difficult to achieve the desired result.

E.g. if the amount of reactant (Y) is below a certain amount, the energy needed in order to achieve the desired increase in temperature might not be produced.

If, however, the amount of reactant (Y) is above a certain amount, the energy generated might result in a not desirable increase of temperature. Especially in the dental area this can be unwanted, as composition with a too high temperature might not be acceptable to the patient during treatment.

If the molecular weight of reactant (Y) is too high, the ability of reactant (Y) to diffuse or migrate within the composition and to interact with other components might be limited.

Reactant (Y) can be present in the base paste or the catalyst paste or in the base paste and the catalyst paste.

In some instances it can be advantageous, if reactant (Y) is present in the base paste only.

This might help reducing the risk that the catalyst being present in the catalyst paste interacts with reactant (Y).

This can also be beneficial if base paste and catalyst paste are used in a mixing ratio being different from 1:1, especially if the base paste is used in a higher amount (e.g. mixing ratio from base paste to catalyst paste being 2:1 or 5:1 or 10:1). By incorporating reactant (Y) only in the base paste, the overall concentration of reactant (Y) in the mixed composition is increased compared to a composition where reactant (Y) is only in the catalyst paste.

With respect to curable compositions hardening by a polycondensation reactions, typical examples for reactant (Y) include anhydrous salts (including oxides, carbonates and sulfates of Li, Na, K, Sr, Mg and Ca) and mixtures thereof.

With respect to curable compositions hardening by a polyaddition reactions, typical examples for reactant (Y) include components with only one moiety selected from vinyl, allyl, >C=CH—CH$_2$—, >C=C(CH$_3$)—CH$_2$—, vinyl ether and mixtures of either of these components ("<" represents two individual bondings).

With respect to polyaddition reactions and in particular with respect to a hydrosilation reaction, using a reactant (Y) which is characterized by at least one of the following features was found to be useful:

Molecular weight: from about 100 to about 1,000 or from about 200 to about 800 or from about 100 to about 500 or from about 100 to about 300;
comprising only Si and C containing moieties;
comprising only one (carbon-carbon) unsaturated silane moiety (e.g. vinyl or allyl);
not comprising polyether moieties (i.e. at least 3 or 4 or 5 repeating units of ether moieties).

Examples of vinyl ether(s) which can be used include vinyl-t-butyl-ether, vinyl-isobutyl-ether, cyclohexyl-vinyl-ether and mixtures thereof.

Examples for unsaturated silane(s) include those of formula (II):

$$R^2R^3C=CR^1—A—SiR_3 \quad (II)$$

wherein

R can be a monovalent alkyl (linear or branched or cycloalkyl) C1-C22, aryl C6-C12, alkoxy (linear or branched or cycloalkoxy) C1-C22, aryloxy C6-C12, O—Si(R$^4$)$_3$ or H (The residue R may include heteroatoms like O, Cl, Br, F or I. The residues R can be different or equal and are preferably selected from methyl, ethyl, propyl, isopropyl, butyl, isobutyl, sec-butyl, tert-butyl, pentyl, hexyl, heptyl, octyl, 2-ethylhexyl, nonyl, decyl, undecyl, dodecyl, tetradecyl, hexadecyl, octadecyl, phenyl, tolyl, cyclohexyl, trimethylsiloxy, triethylsiloxy, tert-butyldimethylsiloxy, methoxy, ethoxy, isopropoxy, butoxy, 3,5,7,9,11,13,15-heptacyclopentyl-pentacyclo[9.5.13,915,15.17,13]octasiloxan-1-yl, 3,5,7,9,11,13,15-heptaisopropyl-pentacyclo[9.5.13,915,15.17,13]octasiloxan-1-yl), R$^1$, R$^2$, R$^3$ can be equal or different and comprise hydrogen or monovalent alkyl (linear or branched or cycloalkyl) C1-C22, aryl, or C6-C12. R$^1$ and R$^2$ or R$^3$ can also combine to a cyclic structure. The residues R$^1$, R$^2$ and R$^3$ may include heteroatoms like O, Cl, Br, F or I. Preferred for R$^1$, R$^2$ and R$^3$ is H.

R$^4$ can be monovalent alkyl (linear or branched or cycloalkyl) C1-C22, aryl C6-C12, wherein two or three of the residues R$^4$ in O—Si(R$^4$)$_3$ can combine to a cyclic or polycyclic structure like a cyclosiloxane or a polycyclic siloxane structure, A is a divalent linear, branched or cyclic hydrocarbon group C1-C12, optionally comprising an aromatic moiety, with at least one methylene group directly attached to the unsaturation, optionally including O-atoms (A is preferably methylene, ethylene, propylene, butylene, hexylene, octylene, nonylene or decylene).

The unsaturated silane compound comprises preferably the structural element >C=CH—CH$_2$— or >C=C(CH$_3$)—CH$_2$—, preferably the structural element H$_2$C=C—CH$_2$— or H$_2$C=C(CH$_3$)—CH$_2$—.

Good results can be achieved if the unsaturated silane compound comprises only one allyl group.

Especially preferred reactants (Y) include

H$_2$C=CH—CH$_2$Si(CH$_3$)$_3$ CAS: [762-72-1]
H$_2$C=CH—(CH$_2$)$_2$Si(CH$_3$)$_3$
H$_2$C=CH—(CH$_2$)$_3$Si(CH$_3$)$_3$
H$_2$C=CH—(CH$_2$)$_4$Si(CH$_3$)$_3$
H$_2$C=CH—(CH$_2$)$_8$Si(CH$_3$)$_3$
H$_2$C=CH—CH$_2$Si(i-CH$_3$H$_7$)$_3$ CAS: [24400-84-8]
H$_2$C=CH—(CH$_2$)$_2$Si(i-C$_3$H$_7$)$_3$
H$_2$C=CH—(CH$_2$)$_3$Si(i-C$_3$H$_7$)$_3$
H$_2$C=CH—(CH$_2$)$_4$Si(i-C$_3$H$_7$)$_3$
H$_2$C=CH—(CH$_2$)$_8$Si(i-C$_3$H$_7$)$_3$
H$_2$C=CH—CH$_2$Si(CH$_3$)$_2$(t-C$_4$H$_9$)
H$_2$C=CH—(CH$_2$)$_2$Si(CH$_3$)$_2$(t-C$_4$H$_9$)
H$_2$C=CH—(CH$_2$)$_3$Si(CH$_3$)$_2$(t-C$_4$H$_9$)
H$_2$C=CH—(CH$_2$)$_4$Si(CH$_3$)$_2$(t-C$_4$H$_9$)
H$_2$C=CH—(CH$_2$)$_8$Si(CH$_3$)$_2$(t-C$_4$H$_9$)
H$_2$C=CH—CH$_2$Si(C$_2$H$_5$)$_3$
H$_2$C=CH—(CH$_2$)$_2$Si(C$_2$H$_5$)$_3$
H$_2$C=CH—(CH$_2$)$_3$Si(C$_2$H$_5$)$_3$
H$_2$C=CH—(CH$_2$)$_4$Si(C$_2$H$_5$)$_3$
H$_2$C=CH—(CH$_2$)$_8$Si(C$_2$H$_5$)$_3$
H$_2$C=CH—CH$_2$Si(CH$_3$)$_2$(n-C$_{18}$H$_{37}$)
H$_2$C=CH—(CH$_2$)$_2$Si(CH$_3$)$_2$(n-C$_{18}$H$_{37}$)
H$_2$C=CH—(CH$_2$)$_3$Si(CH$_3$)$_2$(n-C$_{18}$H$_{37}$)
H$_2$C=CH—(CH$_2$)$_4$Si(CH$_3$)$_2$(n-C$_{18}$H$_{37}$)
H$_2$C=CH—(CH$_2$)$_8$Si(CH$_3$)$_2$(n-C$_{18}$H$_{37}$)
H$_2$C=CH—CH$_2$Si(CH$_3$)$_2$(C$_6$H$_5$)
H$_2$C=CH—(CH$_2$)$_2$Si(CH$_3$)$_2$(C$_6$H$_5$)
H$_2$C=CH—(CH$_2$)$_3$Si(CH$_3$)$_2$(C$_6$H$_5$)
H$_2$C=CH—(CH$_2$)$_4$Si(CH$_3$)$_2$(C$_6$H$_5$)
H$_2$C=CH—(CH$_2$)$_8$Si(CH$_3$)$_2$(C$_6$H$_5$)
H$_2$C=CH—CH$_2$—O—Si(CH$_3$)$_3$
H$_2$C=CH—CH$_2$—O—Si(C$_2$H$_5$)$_3$
H$_2$C=CH—CH$_2$—O—Si(i-C$_3$H$_7$)$_3$
H$_2$C=CH—CH$_2$—O—Si(CH$_3$)$_2$(t-C$_4$H$_9$)
H$_2$C=CH—CH$_2$—O—Si(CH$_3$)$_2$(n-C$_{18}$H$_{37}$)
H$_2$C=CH—CH$_2$—O—Si(CH$_3$)$_2$(C$_6$H$_5$)
H$_2$C=CH—CH$_2$Si(CH$_3$)$_2$—O—Si(CH$_3$)$_3$
H$_2$C=CH—(CH$_2$)$_2$Si(CH$_3$)$_2$—O—Si(CH$_3$)$_3$
H$_2$C=CH—(CH$_2$)$_3$Si(CH$_3$)$_2$—O—Si(CH$_3$)$_3$
H$_2$C=CH—(CH$_2$)$_4$Si(CH$_3$)$_2$—O—Si(CH$_3$)$_3$
H$_2$C=CH—(CH$_2$)$_8$Si(CH$_3$)$_2$—O—Si(CH$_3$)$_3$
H$_2$C=CH—CH$_2$Si(CH$_3$)(—O—Si(CH$_3$)$_3$)$_2$
H$_2$C=CH—(CH$_2$)$_2$Si(CH$_3$)(—O—Si(CH$_3$)$_3$)$_2$
H$_2$C=CH—(CH$_2$)$_3$Si(CH$_3$)(—O—Si(CH$_3$)$_3$)$_2$
H$_2$C=CH—(CH$_2$)$_4$Si(CH$_3$)(—O—Si(CH$_3$)$_3$)$_2$
H$_2$C=CH—(CH$_2$)$_8$Si(CH$_3$)(—O—Si(CH$_3$)$_3$)$_2$
H$_2$C=CH—CH$_2$Si(—O—Si(CH$_3$)$_3$)$_3$
H$_2$C=CH—(CH$_2$)$_2$Si(—O—Si(CH$_3$)$_3$)$_3$
H$_2$C=CH—(CH$_2$)$_3$Si(—O—Si(CH$_3$)$_3$)$_3$
H$_2$C=CH—(CH$_2$)$_4$Si(—O—Si(CH$_3$)$_3$)$_3$
H$_2$C=CH—(CH$_2$)$_8$Si(—O—Si(CH$_3$)$_3$)$_3$
H$_2$C=CH—CH$_2$Si(OCH$_3$)$_3$
H$_2$C=CH—(CH$_2$)$_2$Si(OCH$_3$)$_3$
H$_2$C=CH—(CH$_2$)$_3$Si(OCH$_3$)$_3$
H$_2$C=CH—(CH$_2$)$_4$Si(OCH$_3$)$_3$
H$_2$C=CH—(CH$_2$)$_8$Si(OCH$_3$)$_3$
H$_2$C=CH—CH$_2$Si(OC$_2$H$_5$)$_3$
H$_2$C=CH—(CH$_2$)$_2$Si(OC$_2$H$_5$)$_3$
H$_2$C=CH—(CH$_2$)$_3$Si(OC$_2$H$_5$)$_3$
H$_2$C=CH—(CH$_2$)$_4$Si(OC$_2$H$_5$)$_3$

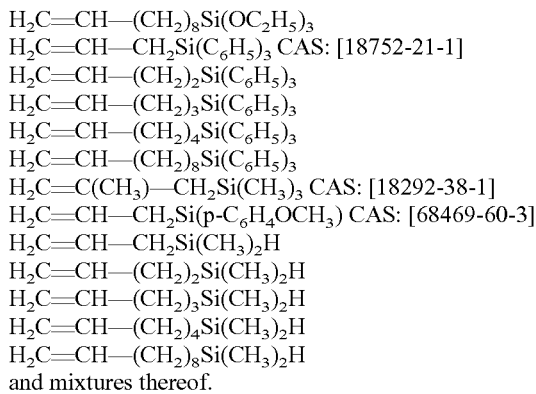

H₂C=CH—(CH₂)₈Si(OC₂H₅)₃
H₂C=CH—CH₂Si(C₆H₅)₃ CAS: [18752-21-1]
H₂C=CH—(CH₂)₂Si(C₆H₅)₃
H₂C=CH—(CH₂)₃Si(C₆H₅)₃
H₂C=CH—(CH₂)₄Si(C₆H₅)₃
H₂C=CH—(CH₂)₈Si(C₆H₅)₃
H₂C=C(CH₃)—CH₂Si(CH₃)₃ CAS: [18292-38-1]
H₂C=CH—CH₂Si(p-C₆H₄OCH₃) CAS: [68469-60-3]
H₂C=CH—CH₂Si(CH₃)₂H
H₂C=CH—(CH₂)₂Si(CH₃)₂H
H₂C=CH—(CH₂)₃Si(CH₃)₂H
H₂C=CH—(CH₂)₄Si(CH₃)₂H
H₂C=CH—(CH₂)₈Si(CH₃)₂H
and mixtures thereof.

The inventive composition may also contain a filler or a mixture of fillers. Typically, filler can be used in an amount of from of at least about 15 wt.-% or at least about 20 or at least about 30 wt.-% with respect to the whole composition.

There is no particular upper limit, however, typically the amount of filler, if present at all, is used in an amount of at most about 70 wt.-% or at most about 60 wt.-% or at most about 50 wt.-% with respect to the whole composition.

Thus, typical ranges for the filler are from about 15 to about 70 or from about 20 to about 60 or from about 30 to about 50 wt.-% with respect to the whole composition.

A wide variety of inorganic, hydrophilic or hydrophobic fillers may be employed such as silicas, aluminas, magnesias, titanias, inorganic salts, metallic oxides and glasses. It has been found to be possible to employ mixtures of silicon dioxides, including those derived from crystalline silicon dioxide, such as pulverized quartz (4-6 μm); amorphous silicon dioxides, such as a diatomaceous earth (4-7 μm); and silanated fumed silica, such as Cab-o-Sil TS-530 (160-240 m²/g), manufactured by Cabot Corporation.

The sizes and surface areas of the foregoing materials can be adjusted to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or alkoxysilanes or silazanes. Such fillers can be present in amounts of from about 0 to about 65% by weight, especially about 5 to about 55 or about 20 to about 50 wt.-% of the material.

Among the fillers which can be used are fillers such as quartz (density 2.65 g/cm³), cristobalite (density 2.35 g/cm³), calcium silicate, diatomaceous earth (density 2.2 g/cm³), zirconium silicate, titanium oxide, barium sulphate, calcium carbonate, plaster, glass and plastic powder.

Suitable fillers are also pyrogenic or precipitated silicic acid and silica aluminium mixed oxides. Those filler are commercially available from companies like Wacker or Degussa under the trade names Aerosil™, HDK-H (density: 2.2 g/cm³ for HDK-H 2000).

The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 μm.

A combination of reinforcing and non-reinforcing fillers can be preferred. In this respect, the quantity of reinforcing fillers can range from about 1 to about 10 wt.-%, in particular from about 2 to about 5 wt.-% with respect to the whole composition.

Typical reinforcing fillers include fumed silica, carbon black and the like. They also can be surface treated and can improve mechanical properties like tensile strength or tear strength, of the cured silicone composition.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Preferred non-reinforcing fillers are quartzes, cristobalites and sodium aluminium silicates which can be surface-treated. The surface treatment can generally be carried out with the same methods as described in the case of the strengthening fillers.

Typical non-reinforcing fillers are quartz, precipitated silicas, diatomaceous earth, aluminas, magnesias, titanium dioxide, zirconium silicate, metallic oxides, and the like. These fillers can be surface treated, e.g. silanated, or non surface treated. Typical particle sizes are about 2 to about 10 μm.

According to a further embodiment, the inventive composition can also contain other additives.

Those additives include rheology modifiers (e.g. synthetic or natural waxes or polyethylene/propylene diacetates as described in EP 1 165 016 A1; corresponding to U.S. Pat. No. 6,677,393), pigments, dyes, plasticizers (including paraffin oil or mineral oil), odorous substances, flavourings, stabilizers (including diphosphite(s) as described e.g. in WO 2007/001896 A2) or hydrogen scavenger etc. alone or in admixture.

The additive(s) can be present in an amount in the range of about 0.01 to about 90% by weight, or in the range of about 0.1 to about 40% by weight with respect to the whole composition.

To control the reactivity of the addition reaction and to prevent premature curing, it may be advantageous to add an inhibitor, which prevents the addition reaction for a specific period of time or slows the addition reaction down. Such inhibitors are known and described, e.g. in U.S. Pat. No. 3,933,880. Examples of such inhibitors include acetylenic unsaturated alcohols such as 3-methyl-1-butyn-3-ol, 1-ethynylcyclohexan-1-ol, 3,5-dimethyl-1-hexyn-3-ol and 3-methyl-1-pentyn-3-ol. Examples of inhibitors based on a vinyl siloxane are 1,1,3,3-tetramethyl-1,3-divinyl siloxane, 1,3,5,7-tetravinyl-1,3,5,7-tetramethylcyclotetrasiloxane and poly-, oligo- and disiloxanes containing vinyl groups. However, if present, the inhibitor should not negatively affect the desired accelerated setting reaction and production of energy.

The composition may also contain a component useful for diminishing the presence or degree of hydrogen outgassing which may be typically generated as a result of the vinyl polymerization. The composition thus may comprise a hydrogen scavenger such as finely divided platinum metal that scavenges for and takes up such hydrogen. The Pt metal may be deposited upon a substantially insoluble salt having a surface area of between about 0.1 and about 40 m²/g. Suitable salts are Barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is about 0.2 to about 2 parts per million of platinum metal, based upon the weight of the catalyst component. It has been found that employment of the platinum metal dispersed upon inorganic salt particles substantially eliminates or diminishes hydrogen outgassing during curing of dental silicones. Also Pd metal as described e.g.

in U.S. Pat. No. 4,273,902 or Pd compounds as disclosed in to U.S. Pat. No. 5,684,060 can be employed.

As a further additive, the inventive composition may comprise a surfactants or hydrophilizing agent.

Surfactants which can be employed can generally be chosen freely from all types of surfactants which improve the hydrophilicity of the composition.

Surfactants, also sometimes referred to as tensides, are wetting agents that are able to lower the surface tension of a liquid, allowing easier spreading, and lower the interfacial tension between two liquids.

Surfactants are usually organic compounds that are amphiphilic, meaning they contain both hydrophobic groups ("tails") and hydrophilic groups ("heads").

A non-ionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitter-ionic.

Useful surfactants include anionic, cationic or non-ionic surfactants or mixtures of two or more of such types of surfactants.

It can be preferred that the composition comprises a non-ionic surfactant as a hydrophilizing agent or a mixture of two or more non-ionic surfactants.

A surfactant is typically capable of increasing the hydrophilic character of a composition. This can be demonstrated, if desired, by an increase in the wetting angle of a drop of water or an aqueous solution or dispersion (e.g. a plaster suspension or the like) on the material (in its cured or uncured state) over that wetting angle achieved on the same composition without surfactant.

A method for measurement of the wetting angle to determine the hydrophilicity of dental impression materials is described e.g. in U.S. Pat. No. 5,569,691, the contents of this document with regard to this method of measurement being expressly mentioned by reference and being regarded as part of the disclosure of the present text.

Ethoxylized fatty alcohols which are e.g. described in EP 0 480 238 B1 can be used. Furthermore, the non-ionic perfluoroalkylated surface-active substances described in U.S. Pat. No. 4,657,959 can be used. Also preferred are the non-ionic surface-active substances which are described in U.S. Pat. No. 4,782,101, i.e. the nonylphenolethoxylates, polyethylene glycol-mono- and diesters, sorbitan esters as well as polyethylene glycol-mono- and diethers listed therein. The contents of the latter documents with regard to hydrophilizing agents and their preparation is expressly mentioned by reference and is regarded as part of the disclosure of the invention.

Suitable hydrophilizing agents can be wetting agents from the group of hydrophilic silicone oils which are not capable of being covalently incorporated into the hardened polymer network. Suitable hydrophilizing agents are described in U.S. Pat. No. 4,657,959 and in EP 0 231 420 B1, the contents of which with regard to the hydrophilizing agents are expressly mentioned by reference and are regarded as part of the disclosure of the invention.

Useful surfactants include polyether carbosilanes of the general formula (III)

$$Q\text{-}P\text{-}(OC_nH_{2n})_x\text{-}OT, \quad (III)$$

in which Q stands for $R_3$-Si— or $R_3$-Si—$(R'$—$SiR_2)_a$-$R'$—$SiR''_2$, where every R in the molecule can be the same or different and stands for an aliphatic $C_1$-$C_{18}$, a cycloaliphatic $C_6$-$C_{12}$ or an aromatic $C_6$-$C_{12}$ hydrocarbon radical, which can optionally be substituted by halogen atoms, R' is a $C_1$-$C_{14}$ alkylene group, R" is R in the case of a≠0 or is R or $R_3SiR'$ in the case of a=0, and a=0-2; P stands for a $C_2$-$C_{18}$ alkylene group, preferably a $C_2$-$C_{14}$ alkylene group or A-R''', where A represents a $C_2$-$C_{18}$ alkylene group and R''' a functional group from the following list: —NHC(O)—, —NHC(O)—$(CH_2)_{n-1}$-, —NHC(O)C(O)—, —NHC(O)$(CH_2)_v$C(O)—, —OC(O)—, —OC(O)—$(CH_2)_{n-1}$-, —OC(O)C(O)—, —OC(O)$(CH_2)_v$C (O)—, —OCH$_2$CH(OH)CH$_2$OC(O$(CH_2)_{n-1}$-, —OCH$_2$CH (OH)CH$_2$OC(O)$(CH_2)_v$C(O)— with v=1-12; T is H or stands for a $C_1$-$C_4$ alkyl radical or a $C_1$-$C_4$ acyl radical; x stands for a number from 1 to 200 and n stands for an average number from 1 to 6, preferably 1 to 4.

The polyether part can be a homopolymer, but can also be a statistical, alternating or block copolymer.

Surfactants which can also be used, either alone or as a mixture of two or more thereof, can be found in U.S. Pat. No. 5,750,589 (Zech et al), col. 2, 1. 47 to col. 3 1. 27 and col. 3,1. 49 to col. 4,1. 4 and col. 5,1. 7 to col. 14,1. 20.

Other surfactants which can be used, either alone or as a mixture of two or more thereof, can be found in U.S. Pat. No. 4,657,959 (Bryan et al.), col. 4, 1. 46 to col. 6. 1. 52 as well as in EP 0 231 420 B1 (Gribi et al.) p4, 1. 1 to p. 5, 1. 16 and in the examples.

U.S. Pat. No. 5,750,589, U.S. Pat. No. 4,657,959 and EP 0 231 420 B1 are expressly described and cited herein as a source of disclosure for compounds which can be used as component (G) according to the invention. The documents and especially their disclosure with regard to hydrophilizers at the citations given above are incorporated by reference and are considered as being a part of the disclosure of the present text.

Further preferred surfactants are ethoxylated surfactants containing a siloxane solubilizing group as described in U.S. Pat. No. 4,657,959, the disclosure of which is incorporated herein by reference.

Some of the surfactants can be summarized under the following formula (IV)

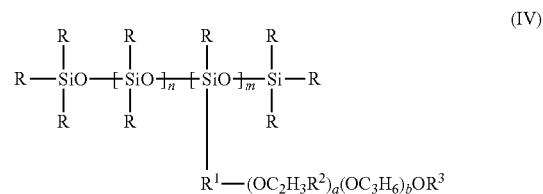

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition the invention has the desired water contact angle.

Preferably R and $R^3$ are —CH$_3$, $R^1$ is —C$_3$H$_6$—, $R^2$ is hydrogen, n is about zero or about one, m is about one to about five, a is about five to about 20 and b is about 0.

Several of such ethoxylated surfactants are available from Union Carbide Corp. as "SILWET" surface active copolymers. Preferred surface active copolymers include SILWET 35, SILWET L-77, L-7600 and L-7602. SILWET L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL® SF19, as obtainable from Lubrizol performance products, Spartanburg, US.

Also possible is the use of polyether carbosilanes selected from the group consisting of:

$Et_3Si$—$(CH_2)_3$—O—$(C_2H_4O)y$—$CH_3$, Et ethyl
$Et_3Si$—$CH_2$—$CH_2$—O—$(C_2H_4O)y$—$CH_3$, Et ethyl
$(Me_3Si$—$CH_2)_3Si$—$(CH_2)_3$—O—$(C_2H_4O)y$—$CH_3$, Me methyl
$Me_3Si$—$CH_2$—$SiMe_2$—$(CH_2)_3$—O—$(C_2H_4O)y$—$CH_3$, Me methyl
$(Me_3Si$—$CH_2)_2SiMe$—$(CH_2)_3$—O—$(C_2H_4O)y$—$CH_3$, Me methyl
$Me_3Si$—$(CH_2)_3$—O—$(C_2H_4O)y$—$CH_3$, Me methyl
$Me_3Si$—$CH_2$—$CH_2$—O—$(C_2H_4O)y$—$CH_3$, Me methyl
$Ph_3Si$—$(CH_2)_3$—O—$(C_2H_4O)y$—$CH_3$, Ph=phenyl
$Ph_3Si$—$CH_2$—$CH_2$—O—$(C_2H_4O)y$—$CH_3$, Ph=phenyl
$Cy_3Si$—$(CH_2)_3$—O—$(C_2H_4O)y$—$CH_3$, Cy=cyclohexyl
$Cy_3Si$—$CH_2$—$CH_2$—O—$(C_2H_4O)y$—$CH_3$, Cy=cyclohexyl
$(C_6H_{13})_3Si$—$(CH_2)_3$—O—$(C_2H_4O)y$—$CH_3$
$(C_6H_{13})_3Si$—$CH_2$—$CH_2$—O—$(C_4H_4O)y$—$CH_3$ in which y conforms to the relation: $5 \leq y \leq 20$.

Surfactants can be present in the composition in an amount of more than about 0.1% by weight, relating to the weight of the whole composition. It can be preferred if the amount of surfactant is in a range of from about 0.1 to about 15% by weight or from about 0.3 to about 12% by weight or from about 0.5 to about 8% by weight or from about 0.8 to about 7% by weight or from about 1 to about 6% by weight or from about 1.2 to about 5% by weight or from about 1.5 to about 4% by weight.

The wetting angle of a drop of water on the surface of a cured material according to the invention measured after 10 seconds, is preferably less than about 40° or less than about 20° or less than about 10° or even less than about 5°.

Wetting contact angles can be measured as follows: About 2.5 g of base and 2.5 g of catalyst paste are mixed together until uniform (about 30 s). 5 g of mixed paste is placed in a metal mould (40 mm×30 mm×2 mm) between two sheets of polyethylene and pressed flat using a glass plate. The specimen is allowed to stand undisturbed until set (about 15 minutes). The polyethylene sheets are removed, being careful not to touch the surface of the specimen, and the specimen placed on the table of a goniometer DSA 10 (Krüss), a well known device for measuring contact angles. 5 µl of water are placed onto the surface of the specimen and an automatic contact angle measurement is started using standard software of the goniometer. Measuring time is at least about 10 s up to about 200 s.

In addition or alternatively to the surfactant(s) mentioned above, the composition may also comprise an F-containing component, wherein the F-containing compound is characterized by formula (V)

$$T_1\text{-}X\text{-}[(O\text{—}CF_2\text{—}CF_2)_u\text{-}(O\text{—}CF_2)_v\text{-}(O\text{—}CF(CF_3)\text{—}CF_2)_w\text{-}(O\text{—}CF_2\text{—}CF_2\text{—}CF_2)_x\text{—}O]\text{-}X\text{-}T_2 \quad (V)$$

with u=0 to 8, v=0 to 8, w=0 to 8 and x=0 to 8 and u+v+w+x≥1, wherein $T_1$ and $T_2$ can be equal or different and are independently selected from —COOR, —$CH_2OH$, —$CF_2OR$, —CHFOH, —CHFOR, —$CH_2OR$ or —F with R being a linear or branched alkyl rest (C1 to C9), aryl rest (C1 to C9) or alkylaryl rest (C1 to C9), and wherein X is selected from —$(CF_2)_{1-6}$-, —$CF(CF_3)$— and —CHF—$CF_2$—.

Useful F-containing compound also include those being characterized by formula (VI)

$$T_1\text{-}X\text{-}[(O\text{—}CF_2\text{—}CF_2)_u\text{-}(O\text{—}CF_2)_v\text{-}(O\text{—}CF(CF_3)\text{—}CF_2)_w\text{-}(O\text{—}CF_2\text{—}CF_2\text{—}CF_2)_x\text{—}O]\text{-}X\text{-}T_2 \quad (VI)$$

with u=0 to 8, v=0 to 8, w=0 to 8 and x=0 to 8 and u+v+w+x≥1, wherein $T_1$ and $T_2$ can be equal or different and are independently selected from —COOR, —$CH_2OH$, —$CF_2OR$, —CHFOH, —CHFOR, —$CH_2OR$ or —F with R being a linear or branched alkyl rest (C1 to C9), aryl rest (C1 to C9) or alkylaryl rest (C1 to C9), and wherein X is selected from —$(CF_2)_{1-6}$-, —$CF(CF_3)$— and —CHF—$CF_2$—.

If present, the F-containing component can be present in an amount below about 5 or below about 4 wt.-% with respect to the amount of the whole composition.

Typical ranges for the F-containing component include from about 0 to about 5, or from about 0.1 to about 4 wt.-% with respect to the amount of the whole composition.

It can be preferred if the F-containing component is present together with a surfactant as described above. The presence of both components might lead to an improved wettability of the composition.

According to one embodiment, the inventive composition can comprise the individual components in the following amounts:

Components (A) in an amount from about 15 to about 70 wt.-% or from about or from about 20 to about 60 wt.-%,
Catalyst in an amount from about 0.00005 to about 35 wt.-% or from about 0.0002 to about 20 wt.-%,
Reactant (Y) in an amount from about 0.5 to about 6 wt.-% or from about or from about 1 to about 5 wt.-% or from about 1.25 to about 4 wt.-%,
Filler in an amount from about 15 to about 70 wt.-% or from about 20 to about 60 wt.-% or from about 30 to about 50 wt.-%,
Additives in an amount from about 0 to about 65 wt.-% or from about 0.1 to about 40 wt.-%, wt.-% with respect to the weight of the whole composition.

With respect to dental compositions curing by a polyaddition reaction, the following amounts were found to be useful:

Components (A) in an amount from about 10 to about 60 wt.-% or from about or from about 15 to about 55 wt.-%, or from about 20 to about 50 wt.-%,
Catalyst in an amount from about 0.00005 to about 0.1 wt.-% or from about 0.0002 to about 0.02 wt.-% or from about 0.005 to about 0.01 wt.-% (based on Pt-content),
Reactant (Y) in an amount from about 0.1 to about 20 wt.-% or from about or from about 0.2 to about 10 wt.-% or from about 0.3 to about 5 wt.-%,
Filler in an amount from about 5 to about 85 wt.-% or from about 10 to about 80 wt.-% or from about 20 to about 75 wt.-%,
Additives in an amount from about 0 to about 50 wt.-% or from about 1 to about 30 wt.-% or from about 2 to about 20 wt.-%, wt.-% with respect to the weight of the whole composition.

According to a particular embodiment, the inventive curable dental composition can be characterized as follows (Polycondensation):

Base paste comprising: components with alkoxy silyl groups and/or with silanol groups;
Catalyst paste comprising: acid and/or metal organic compounds;
Reactant (Y) comprising: anhydrous metal salts and mixtures thereof.

According to another particular embodiment the inventive curable dental composition can be characterized as follows (Polyaddition):

Base paste comprising: divinyl terminated polydimethylsiloxane, poly(methyl)(hydrogen)siloxane and filler;

Catalyst paste comprising: Pt containing component, a divinyl terminated polydimethylsiloxane and filler;

Reactant (Y) comprising: silane component containing only one terminal (carbon-carbon) unsaturated moiety, an alkyl (e.g. C1 to C10) vinyl ether component, an alkyl (e.g. C1 to C10) allyl ether component and mixtures thereof;

Reactant (Y) is typically present in an amount of about 1 to about 5 wt.-% or in an amount of about 1.25 to about 4 wt.-% with respect to the weight of the whole composition.

Due to the higher molar amount of hydrogen siloxane crosslinker (corresponding to component (X)) compared to the amount of reactant (Y), the portion of the hydrogen siloxane crosslinker not participating in the crosslinking reaction can interact with reactant (Y) and thereby generate additional energy which will contribute to the temperature increase.

If the ratio is not within the proper range, the other desired physical properties of the cured composition might be negatively affected.

The composition is typically able to produce energy in an amount sufficient to increase the temperature T1 of the composition being present 20 s after mixing the base paste and the catalyst paste to a temperature T2 being from about 6 to about 20° C. above T1.

The base paste and the catalyst paste of the inventive curable composition are typically produced by mixing the individual components. Mixing means include blending and/or kneading. If desired, mixing can be effected under vacuum conditions to ensure a more homogeneous and gas free composition.

The dental compositions according to the invention are typically multi component materials which comprise at least a base paste and a catalyst paste comprising a catalyst for curing at least part of the material of the base paste.

The components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base part (I) and a catalyst part (II) separated from each other before use, wherein the base part (I) comprises curable component(s) (A), and the catalyst part (II) comprises a catalyst, and wherein reactant (Y) is present either in the base part or the catalyst part.

The other optional components, especially filler and additives can be present in the base part (I) or the catalyst part (II) or in the base part (I) and the catalyst part (II).

The volume ratios of catalyst part (II) and base part (I) can range from about 10:1 to about 1:10. Particularly preferred volume ratios of base part (I) to catalyst part (II) are about 1:1 and about 5:1 (5 parts of base part to 1 part of catalyst part).

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. No. 5,924,600, U.S. Pat. No. 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as described e.g. in U.S. Pat. No. 5,249,862, U.S. Pat. No. 5,286,105 or U.S. Pat. No. 5,332,122. The result after mixing the respective pastes is usually a homogeneous product which is essentially free of air bubbles. Commercially available mixing devices are distributed by 3M ESPE under the brand Pentamix™.

In practice, the impression material can be syringed through a static or mechanical mixing device into an impression tray or onto patient's teeth or tissue and placed in the patient's mouth. After the impression material is set, the tray is typically removed from the patient's mouth and, in instances where the dental practitioner prepares a positive model, it may be desirable to pour the negative model e.g., with plaster.

The dental material or composition can be used as dental impression material or for the production of (temporary or long term) crown and/or bridges. In the latter case, the inventive composition is used as a mould to be filled with the (temporary or long term) crown and/or bridge material, which is typically based on polymerizable (meth)acrylates.

Features and advantages of this invention are further illustrated by the following examples, which are in no way intended to be limiting thereof. Unless otherwise indicated, all parts and percentages are on a weight basis, all water is deionized water, and all molecular weights are weight average molecular weight.

EXAMPLES

Measurements

Tensile Strength and Elongation at Break

If desired, the tensile strength and elongation of the compositions can be determined according to DIN 53504. The tensile strength is given in MPa and the elongation in % of the original length. Tensile strength and elongation data were evaluated by tearing six I-shaped specimens with a central unit of 20 mm×4 mm×2 mm in a Zwick Z020 Universal testing machine. Base and catalyst pastes are mixed through a static mixer (SulzerMixpac Comp.) and filled into a brass mould. After 3 h at 23° C. the specimen are removed, six measurements are made and the mean value determined (speed 200 mm/min).

Linear Dimensional Change

If desired, the linear dimensional change of the compositions can be determined according to ISO 4823 and is given in %.

Viscosity

If desired, the viscosity can be measured at 23° C. using a Haake Rotovisco 1 device with a plate/plate system (diameter 20 mm) and a slit of 0.2 mm. The viscosity values (Pas) and share stress values (Pa) are recorded for each share rate (starting from 10 1/s to 100 1/s in 10 1/s and/or 5 1/s steps. For each share rate, a delay of 5 seconds was used before collecting data. The above mentioned method of measurement corresponds essentially to DIN 53018-1.

Determination of Setting Time

The setting time of the compositions was determined by measuring the viscosity in dependence on the time at 33° C. by using a MDR 2000 rheometer from Alpha instruments. The setting time was determined as the t90 value, at which 90% of the final viscosity was achieved (from start of mixing). Another characteristic size is the t5 value, at which 5% of the final viscosity was present. Until this time the composition can be assumed to be almost free of network formation (curing).

The difference Δt between the curing time t90 and working time t5 was calculated according to Δt=t90−t5 and reflects the transition time from plastic to the elastic state of the material. The ratio of working time t5 and transition time Δt of the material is a measure of the so-called snap set curing behaviour of the material.

Determination of Temperature Evolution

Base paste and catalyst were mixed and 5 g of the mixed material was placed on a mixing pad. The tip of the temperature sensor of an electronic thermometer (testo 720; testo AG) was placed in the material and the temperature was measured. The first measurement point was recorded 1:00 min after start of mixing in 30 s intervals. The temperature difference ΔT can be calculated as the difference between the maximum temperature $T_{max}$ and the measured room temperature.

Determination of Shore Hardness A in Dependency of the Time

The Shore hardness A of the compositions was determined according to DIN 53 505 and measured at defined times after mixing of the base and catalyst paste. The Shore hardness of the composition was measured during the setting reaction in 30 sec interval. The first measurement was done as soon as the foil can be removed and the last point was measured 10 min after start of mixing the base and catalyst paste. The relative Shore hardness A was calculated by the dividing the Shore hardness A by value at 10 min. The relative Shore hardness A in dependence of the time is shown in FIG. 1.

The time difference $\Delta t^{SH}$ was calculated as the difference between the time at which the first data point was measurable and the time at which 90% of the 10 min Shore hardness A was reached.

Preparation of Compositions

The base and catalyst paste used hereafter were prepared in a vacuum kneader by mixing the respective components to a homogenous paste.

Base Paste A:

| | |
|---|---|
| Mixture of vinyl terminated polydimethylsiloxane (8,000 mPas) | 40.7 wt.-% |
| Poly(methyl)(hydrogen)siloxane (50 mPas, 1.8 mmol/g SiH) | 5.7 wt.-% |
| Poly(methyl)(hydrogen)siloxane (100 mPas, 4.0 mmol/g SiH) | 11.9 wt.-% |
| Pyrogenic silica (hydrobized, 100 m²/g) | 2.6 wt.-% |
| Crystalline SiO₂ filler (<20 μm) | 36.1 wt.-% |
| Surfactant | 3.1 wt.-% |

3 wt.-% of Reactant (Y) were added to the base paste A and kneaded to obtain a homogenous paste (Table 1, Base paste B and C).

Base Paste D:

| | |
|---|---|
| Mixture of vinyl terminated polydimethylsiloxane (8,000 mPas) | 39.5 wt.-% |
| Poly(methyl)(hydrogen)siloxane (50 mPas, 1.8 mmol/g SiH) | 5.5 wt.-% |
| Poly(methyl)(hydrogen)siloxane (100 mPas, 4.0 mmol/g SiH) | 11.5 wt.-% |
| Pyrogenic silica (hydrophobized, 100 m²/g) | 2.5 wt.-% |
| Crystalline SiO₂ filler (<20 μm) | 35.5 wt.-% |
| Surfactant | 3.0 wt.-% |
| Allyltrimethylsilane (Reactant (Y)) | 2.5 wt-% |

Base Paste E:

| | |
|---|---|
| Mixture of vinyl terminated polydimethylsiloxane (8,000 mPas) | 38.5 wt.-% |
| Poly(methyl)(hydrogen)siloxane (50 mPas, 1.8 mmol/g SiH) | 4.5 wt.-% |
| Poly(methyl)(hydrogen)siloxane (100 mPas, 4.0 mmol/g SiH) | 11.0 wt.-% |
| Pyrogenic silica (hydrophobized, 100 m²/g) | 2.5 wt.-% |
| Crystalline SiO₂ filler (<20 μm) | 35.5 wt.-% |
| Surfactant | 3.0 wt.-% |
| Allyl tris(trimethylsiloxy)silane (Reactant (Y)) | 5.0 wt.-% |

Base Paste F:

| | |
|---|---|
| Mixture of vinyl terminated polydimethylsiloxane (8,000 mPas) | 47.5 wt.-% |
| Poly(methyl)(hydrogen)siloxane (50 mPas, 1.8 mmol/g SiH) | 5.5 wt.-% |
| Poly(methyl)(hydrogen)siloxane (100 mPas, 4.0 mmol/g SiH) | 6.0 wt.-% |
| Pyrogenic silica (hydrophobized, 100 m²/g) | 2.5 wt.-% |
| Crystalline SiO₂ filler (<20 μm) | 35.5 wt.-% |
| Surfactant | 3.0 wt.-% |

Base Paste G: (cf. Example D of U.S. Pat. No. 7,700,712 B2)

| | |
|---|---|
| Mixture of vinyl terminated polydimethylsiloxane (4,000 mPas) | 43.8 wt.-% |
| Poly(methyl)(hydrogen)siloxane (50 mPas, 1.8 mmol/g SiH) | 6.0 wt.-% |
| Poly(methyl)(hydrogen)siloxane (100 mPas, 4.0 mmol/g SiH) | 7.0 wt.-% |
| Pyrogenic silica (hydrophobized, 100 m²/g) | 4.0 wt.-% |
| Hydrophobized crystalline SiO₂ filler (<20 μm) | 29.5 wt.-% |
| Silicone oil (10 mPas) | 7.8 wt.-% |
| Pigment | 0.5 wt.-% |
| Surfactant | 1.5 wt.-% |

Base Paste H (for 5:1) (cf. Example A of U.S. Pat. No. 7,700,712 B2):

| | |
|---|---|
| Mixture of vinyl terminated polydimethylsiloxane (650 mPas) | 27.2 wt.-% |
| Poly(methyl)(hydrogen)siloxane (200 mPas, 1.8 mmol/g SiH) | 7.4 wt.-% |
| Pyrogenic silica (hydrophobized, 100 m²/g) | 6.4 wt.-% |
| Hydrophobized crystalline SiO₂ filler (<20 μm) | 56.1 wt.-% |
| Pigment dispersion | 1.0 wt.-% |
| Allyltrimethylsilane (Reactant (Y)) | 1.5 wt.-% |
| Surfactant | 0.4 wt.-% |

Catalyst Paste A:

| | |
|---|---|
| Mixture of divinyl terminated polydimethylsiloxane (5,800 mPas) | 49.1 wt-% |
| tetraallylsilane | 0.5 wt.-% |
| platinum tetramethyldivinyldisiloxane complex (3.5% VMO) | 1.6 wt.-% |
| palladium chloride dispersion in divinylpolydimethylsiloxane (2,000 mPas) | 0.1 wt.-% |
| pigment | 0.6 wt.-% |
| pyrogenic silica (hydrophobized 100 m²/g) | 3.5 wt.-% |
| crystalline SiO₂ filler (<20 μm) | 44.6 wt.-% |

Catalyst Paste B:

| | |
|---|---|
| Mixture of divinyl terminated polydimethylsiloxane (5,800 mPas) | 49.1 wt-% |
| tetraallylsilane | 0.5 wt.-% |
| platinum tetramethyldivinyldisiloxane complex (5% VMO) | 1.6 wt.-% |

-continued

| | |
|---|---|
| palladium chloride dispersion in divinylpolydimethylsiloxane (2,000 mPas) | 0.1 wt.-% |
| pigment | 0.6 wt.-% |
| pyrogenic silica (hydrophobized 100 m²/g) | 3.5 wt.-% |
| crystalline SiO₂ filler (<20 μm) | 44.6 wt.-% |

Catalyst Paste C:

| | |
|---|---|
| Mixture of divinyl terminated polydimethylsiloxane (4,800 mPas) | 40.7 wt.-% |
| tetraallylsilane | 0.5 wt.-% |
| platinum tetramethyldivinyldisiloxane complex | 1.6 wt.-% |
| pigment | 0.1 wt.-% |
| silicone oil (10 mPas) | 3.8 wt.-% |
| pyrogenic silica (hydrophobized 100 m²/g) | 2.6 wt.-% |
| crystalline SiO₂ filler (<20 μm) | 49.9 wt.-% |
| Allyltrimethylsilane (Reactant (Y)) | 0.8 wt.-% |

Catalyst Paste D (for 5:1):

| | |
|---|---|
| Divinyl terminated polydimethylsiloxane (200 mPas) | 30.0 wt-% |
| platinum tetramethyldivinyldisiloxane complex (3.5% VMO) | 4.0 wt.-% |
| palladium chloride dispersion in divinylpolydimethylsiloxane (2,000 mPas) | 0.1 wt.-% |
| pigment dispersion | 1.5 wt.-% |
| pyrogenic silica (hydrophobized 100 m²/g) | 5.0 wt.-% |
| Sodium aluminum silicate | 59.5 wt.-% |

TABLE 1

| | | | Reactant Y | wt.-% | Ratio (*) |
|---|---|---|---|---|---|
| Base paste B | Catalyst paste A | Example 1 | Allyltrimethylsilane | 1.5 | 2.14 |
| Base paste C | Catalyst paste A | Example 2 | Vinyl-t-butyl-ether | 1.5 | 1.82 |
| Base paste D | Catalyst paste A | Example 3 | Allyltrimethylsilane | 1.25 | 2.55 |
| Base paste E | Catalyst paste B | Example 4 | Allyl tris-(trimethylsiloxy)silane | 2.5 | 3.51 |
| Base paste F | Catalyst paste A | C. E. 1 | | | n.a. |
| Base paste G | Catalyst paste C | C. E. 2 | Allyltrimethylsilane | 0.4 | 5.54 |
| Base paste H | Catalyst paste D | C. E. 3 | Allyltrimethylsilane | 1.25 | 1.01 |

(*) molar ratio of reactive moieties in component (X) to reactant (Y)

The base paste B, C, D, E, F or G, respectively, and Catalyst Paste A, B or C, respectively were filled in a dual chamber cartridge (SulzerMixpac Comp.), volume ratio 1:1, equipped with a static mixing tip (SulzerMixpac Company). The pastes were extruded from the cartridge and mixed using a hand mixing apparatus (3M ESPE Comp.).

Base H and catalyst paste C were mixed in the ratio 5:1 with a spatula by hand.

The Shore hardness of the compositions during the setting reaction at room temperature was determined and is shown in FIG. 1 and the time $\Delta t^{SH}$ for Examples 2-4 are summarized in Table 2.

The setting properties of the material and the temperature development over the curing time were determined and are summarized in Tables 3 and 4.

TABLE 2

| | $\Delta t^{SH}$ |
|---|---|
| C. E. 1 | 3.5 |
| C. E. 2 | 3.5 |
| Example 1 | 1.5 |
| Example 2 | 2.0 |
| Example 3 | 2.0 |

TABLE 3

| | t5 | t90 | Δt |
|---|---|---|---|
| C. E. 1 | 1.92 | 3.49 | 1.57 |
| C. E. 2 | 1.48 | 3.47 | 1.99 |
| C. E. 3 | 3.51 | 6.77 | 3.26 |
| Example 1 | 1.69 | 2.30 | 0.75 |
| Example 2 | 1.01 | 1.75 | 0.74 |
| Example 3 | 1.29 | 1.99 | 0.70 |
| Example 4 | 1.96 | 3.19 | 1.23 |

TABLE 4

| | t ($T_{max}$) [min] | $T_{max}$ [° C.] | ΔT [° C.] |
|---|---|---|---|
| C. E. 1 | 8.5 | 26.2 | 3.0 |
| C. E. 2 | 6.5 | 28.7 | 5.8 |
| C. E. 3 | 12.0 | 26.6 | 2.9 |
| Example 1 | 5.0 | 31.6 | 7.9 |
| Example 2 | 5.0 | 31.6 | 7.6 |
| Example 3 | 5.0 | 31.2 | 8.2 |
| Example 4 | 8.0 | 30.5 | n.m |

As can be seen from Table 2-4 and FIG. 1, the setting time of the compositions used in Examples 1-4 is reduced compared to the composition of Comparative Examples 1 and 2 (C.E.).

The invention claimed is:

1. A curable dental composition being prepared by mixing a base paste and a catalyst paste,
the base paste comprising component(s) (A) with curable moieties (AC) selected from a combination of at least one organopolysiloxane with at least 2 aliphatically unsaturated groups and at least a component comprising Si—H moieties,
the catalyst paste comprising a catalyst (C) comprising a Pt containing component,
the curable composition comprising a component (X) comprising at least one Si—H group as reactive moiety, component (X) being present in the base paste,
either base paste or catalyst paste comprising a reactant (Y), reactant (Y) being able to interact with component (X), but not taking part in a crosslinking reaction,
reactant (Y) being selected from a silane component with only one unsaturated moiety, an alkyl vinyl ether component, an alkyl allyl ether component and mixtures thereof,
the molar ratio of the reactive moieties of component (X) to reactant (Y) being from 1.2 to 5,
component (A) being present in an amount from 15 to 70 wt.-% with respect to the weight of the whole composition,
catalyst (C) being present from 0.00005 to 35 wt.% with respect to the weight of the whole composition, reactant (Y) being present from 0.5 to 6 wt.-% with respect
to the weight of the whole composition, the curable composition being able to produce energy in an
amount sufficient to increase the temperature T1 of the
composition measured 20 s after mixing the base paste
and the catalyst paste to a temperature T2 being from
about 6 to about 20° C. above T1.

2. The composition according to claim 1 being characterized by at least one of the following features after curing:
a tensile strength (according to DIN 53504) of about 0.1 to about 5 MPa,
an elongation at break (according to DIN 53 504) of about 10 to about 300%,
a Shore A hardness (according to IN 53 505) of about 15 to about 75,
a recovery from deformation (according to ISO 4823): at least about 90%,
a density (according to the Archimedes method; weight of 1 ml cured composition) of the composition of about 0.8 to about 2 g/ml.

3. The composition according to claim 1, the composition being characterized by at least one of the following features before or during curing:
a consistency (according to ISO 4823) of 0 or 1 (corresponding to at most 35 mm) or 2 (corresponding to 31 mm to 41 mm) or 3 (corresponding to at least 36 mm); and/or
a setting time within about 15 or about 10 min after mixing at ambient conditions.

4. The composition according to claim 1, reactant (Y) being characterized by at least one of the following features:
molecular weight: from about 50 to about 1,000;
being solid or liquid at room temperature;
being present in an amount of at least 0.5 wt.-% with respect to the whole composition;
ratio of component (X) to reactant (Y): from about 6:1 to 20:1 with respect to weight.

5. The composition according to claim 1, reactant (Y) being a silane component with only one unsaturated moiety, the unsaturated moiety being selected from vinyl, allyl, vinyl ether, allyl ether, >C=CH—CH$_2$— or >C=C(CH$_3$)—CH$_2$—.

6. The composition according to claim 1, reactant (Y) being characterized by the following formula $$R^2R^3C=CR^1—A—SiR_3$$

wherein
R being a monovalent alkyl, aryl, alkoxy, aryloxy group, O—SiR$^4_3$ or H, wherein the residue R may include heteroatoms selected from O, Cl, Br, F and I, the residues R being different or equal,
R$^1$, R$^2$, R$^3$ being equal or different and comprising hydrogen or monovalent alkyl, aryl wherein the residues R$^1$, R$^2$ and R$^3$ may include heteroatoms selected from O, Cl, Br, F, I,
R$^4$ being alkyl or aryl, wherein two or three of the residues R$^4$ in O—SiR$^4_3$ can combine to a cyclic or polycyclic structure,
A being a divalent linear, branched or cyclic hydrocarbon group, optionally comprising an aromatic moiety, with at least one methylene group directly attached to the unsaturation.

7. The composition according to claim 1, reactant (Y) being selected from

H$_2$C=CH—CH$_2$Si(CH$_3$)$_3$
H$_2$C=CH—(CH$_2$)$_2$Si(CH$_3$)$_3$
H$_2$C=CH—(CH$_2$)$_3$Si(CH$_3$)$_3$
H$_2$C=CH—(CH$_2$)$_4$Si(CH$_3$)$_3$
H$_2$C=CH—(CH$_2$)$_8$Si(CH$_3$)$_3$
H$_2$C=CH—CH$_2$Si(i-CH$_3$H$_7$)$_3$
H$_2$C=CH—(CH$_2$)$_2$Si(i-C$_3$H$_7$)$_3$
H$_2$C=CH—(CH$_2$)$_3$Si(i-C$_3$H$_7$)$_3$
H$_2$C=CH—(CH$_2$)$_4$Si(i-C$_3$H$_7$)$_3$
H$_2$C=CH—(CH$_2$)$_8$Si(i-C$_3$H$_7$)$_3$
H$_2$C=CH—CH$_2$Si(CH$_3$)$_2$(t-C$_4$H$_9$)
H$_2$C=CH—(CH$_2$)$_2$Si(CH$_3$)$_2$(t-C$_4$H$_9$)
H$_2$C=CH—(CH$_2$)$_3$Si(CH$_3$)$_2$(t-C$_4$H$_9$)
H$_2$C=CH—(CH$_2$)$_4$Si(CH$_3$)$_2$(t-C$_4$H$_9$)
H$_2$C=CH—(CH$_2$)$_8$Si(CH$_3$)$_2$(t-C$_4$H$_9$)
H$_2$C=CH—CH$_2$Si(C$_2$H$_5$)$_3$
H$_2$C=CH—(CH$_2$)$_2$Si(C$_2$H$_5$)$_3$
H$_2$C=CH—(CH$_2$)$_3$Si(C$_2$H$_5$)$_3$
H$_2$C=CH—(CH$_2$)$_4$Si(C$_2$H$_5$)$_3$
H$_2$C=CH—(CH$_2$)$_8$Si(C$_2$H$_5$)$_3$
H$_2$C=CH—CH$_2$Si(CH$_3$)$_2$(n-C$_{18}$H$_{37}$)
H$_2$C=CH—(CH$_2$)$_2$Si(CH$_3$)$_2$(n-C$_{18}$H$_{37}$)
H$_2$C=CH—(CH$_2$)$_3$Si(CH$_3$)$_2$(n-C$_{18}$H$_{37}$)
H$_2$C=CH—(CH$_2$)$_4$Si(CH$_3$)$_2$(n-C$_{18}$H$_{37}$)
H$_2$C=CH—(CH$_2$)$_8$Si(CH$_3$)$_2$(n-C$_{18}$H$_{37}$)
H$_2$C=CH—CH$_2$Si(CH$_3$)$_2$(C$_6$H$_5$)
H$_2$C=CH—(CH$_2$)$_2$Si(CH$_3$)$_2$(C$_6$H$_5$)
H$_2$C=CH—(CH$_2$)$_3$Si(CH$_3$)$_2$(C$_6$H$_5$)
H$_2$C=CH—(CH$_2$)$_4$Si(CH$_3$)$_2$(C$_6$H$_5$)
H$_2$C=CH—(CH$_2$)$_8$Si(CH$_3$)$_2$(C$_6$H$_5$)
H$_2$C=CH—CH$_2$—O—Si(CH$_3$)$_3$
H$_2$C=CH—CH$_2$—O—Si(C$_2$H$_5$)$_3$
H$_2$C=CH—CH$_2$—O—Si(i-C$_3$H$_7$)$_3$
H$_2$C=CH—CH$_2$—O—Si(CH$_3$)$_2$(t-C$_4$H$_9$)
H$_2$C=CH—CH$_2$—O—Si(CH$_3$)$_2$(n-C$_{18}$H$_{37}$)
H$_2$C=CH—CH$_2$—O—Si(CH$_3$)$_2$(C$_6$H$_5$)
H$_2$C=CH—CH$_2$Si(CH$_3$)$_2$—O—Si(CH$_3$)$_3$
H$_2$C=CH—(CH$_2$)$_2$Si(CH$_3$)$_2$—O—Si(CH$_3$)$_3$
H$_2$C=CH—(CH$_2$)$_3$Si(CH$_3$)$_2$—O—Si(CH$_3$)$_3$
H$_2$C=CH—(CH$_2$)$_4$Si(CH$_3$)$_2$—O—Si(CH$_3$)$_3$
H$_2$C=CH—(CH$_2$)$_8$Si(CH$_3$)$_2$—O—Si(CH$_3$)$_3$
H$_2$C=CH—CH$_2$Si(CH$_3$)(—O—Si(CH$_3$)$_3$)$_2$
H$_2$C=CH—(CH$_2$)$_2$Si(CH$_3$)(—O—Si(CH$_3$)$_3$)$_2$
H$_2$C=CH—(CH$_2$)$_3$Si(CH$_3$)(—O—Si(CH$_3$)$_3$)$_2$
H$_2$C=CH—(CH$_2$)$_4$Si(CH$_3$)(—O—Si(CH$_3$)$_3$)$_2$
H$_2$C=CH—(CH$_2$)$_8$Si(CH$_3$)(—O—Si(CH$_3$)$_3$)$_2$
H$_2$C=CH—CH$_2$Si(—O—Si(CH$_3$)$_3$)$_3$
H$_2$C=CH—(CH$_2$)$_2$Si(—O—Si(CH$_3$)$_3$)$_3$
H$_2$C=CH—(CH$_2$)$_3$Si(—O—Si(CH$_3$)$_3$)$_3$
H$_2$C=CH—(CH$_2$)$_4$Si(—O—Si(CH$_3$)$_3$)$_3$
H$_2$C=CH—(CH$_2$)$_8$Si(—O—Si(CH$_3$)$_3$)$_3$
H$_2$C=CH—CH$_2$Si(OCH$_3$)$_3$
H$_2$C=CH—(CH$_2$)$_2$Si(OCH$_3$)$_3$
H$_2$C=CH—(CH$_2$)$_3$Si(OCH$_3$)$_3$
H$_2$C=CH—(CH$_2$)$_4$Si(OCH$_3$)$_3$
H$_2$C=CH—(CH$_2$)$_8$Si(OCH$_3$)$_3$
H$_2$C=CH—CH$_2$Si(OC$_2$H$_5$)$_3$
H$_2$C=CH—(CH$_2$)$_2$Si(OC$_2$H$_5$)$_3$
H$_2$C=CH—(CH$_2$)$_3$Si(OC$_2$H$_5$)$_3$
H$_2$C=CH—(CH$_2$)$_4$Si(OC$_2$H$_5$)$_3$
H$_2$C=CH—(CH$_2$)$_8$Si(OC$_2$H$_5$)$_3$
H$_2$C=CH—CH$_2$Si(C$_6$H$_5$)$_3$
H$_2$C=CH—(CH$_2$)$_2$Si(C$_6$H$_5$)$_3$
H$_2$C=CH—(CH$_2$)$_3$Si(C$_6$H$_5$)$_3$
H$_2$C=CH—(CH$_2$)$_4$Si(C$_6$H$_5$)$_3$
H$_2$C=CH—(CH$_2$)$_8$Si(C$_6$H$_5$)$_3$
H$_2$C=C(CH$_3$)—CH$_2$Si(CH$_3$)$_3$
H$_2$C=CH—CH$_2$Si(p-C$_6$H$_4$OCH$_3$)
H$_2$C=CH—CH$_2$Si(CH$_3$)$_2$H
H$_2$C=CH—(CH$_2$)$_2$Si(CH$_3$)$_2$H $H_2C=CH-(CH_2)_3Si(CH_3)_2H$
$H_2C=CH-(CH_2)_4Si(CH_3)_2H$
$H_2C=CH-(CH_2)_8Si(CH_3)_2H$
and mixtures thereof.

8. The composition according to claim 1 further comprising at least one of filler(s) or additive selected from hydrophilating agent(s), colourant(s), dye(s), pigment(s), flavourant(s), stabilizer(s), hydrogen scavenger(s) and mixtures thereof.

9. The composition according to claim 1 further comprising a F-containing component, wherein the F-containing compound is characterized by the following formula

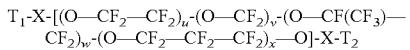
$$T_1\text{-}X\text{-}[(O\text{-}CF_2\text{-}CF_2)_u\text{-}(O\text{-}CF_2)_v\text{-}(O\text{-}CF(CF_3)\text{-}CF_2)_w\text{-}(O\text{-}CF_2\text{-}CF_2\text{-}CF_2)_x\text{-}O]\text{-}X\text{-}T_2$$

with u=0 to 8, v=0 to 8, w=0 to 8 and x=0 to 8 and u+v+w+x≥1, wherein $T_1$ and $T_2$ can be equal or different and are independently selected from —COOR, —CH$_2$OH, —CF$_2$OR, —CHFOH, —CHFOR, —CH$_2$OR or —F with R being a linear or branched alkyl rest (C1 to C9), aryl rest (C1 to C9) or alkylaryl rest (C1 to C9), and wherein X is selected from —(CF$_2$)$_{1-6}$-, —CF(CF$_3$)— and —CHF—CF$_2$—.

10. The composition according to claim 1 comprising:
Component(s) (A): from about 20 to about 60 wt.-%,
Catalyst (C): from about 0.00005 to about 35 wt.-%,
Component (X): from about 5 to about 25 wt.-%,
Reactant (Y): from about 1 to about 5 wt.-%,
Filler(s): from about 0 to about 70 wt.-%,
Additive(s): from about 0 to about 30 wt.-%,
wt.-% with respect to the weight of the whole composition.

11. The composition according to claim 1 being contained in a kit of parts, wherein base paste is present in one container and catalyst paste is present in another container.

12. The composition according to claim 1, the base paste comprising:
at least one organopolysiloxane with at least 2 aliphatically unaturated groups and
at least a component comprising SiH moieties,
the catalyst paste comprising a Pt containing component,
reactant (Y) being a silane containing one unsaturated moiety selected from vinyl or allyl.

13. A process of producing a dental impression material, the process comprising the step of mixing a base paste and a catalyst paste as described in claim 1, the mixture of base paste and catalyst paste having a temperature T1 measured 20 s after mixing, and having a temperature T2 measured within a time frame of 15 min after mixing, T2 being from about 6 to about 20° C. above T1.

* * * * *